United States Patent [19]

Russo

[11] Patent Number: 4,534,542
[45] Date of Patent: Aug. 13, 1985

[54] SUCTION CONTROL DEVICE FOR ASPIRATOR SYSTEM

[75] Inventor: Ronald D. Russo, Barrington, R.I.

[73] Assignee: Superior Plastic Products Corp., Cumberland, R.I.

[21] Appl. No.: 558,575

[22] Filed: Dec. 5, 1983

[51] Int. Cl.³ .............................................. A61M 1/00
[52] U.S. Cl. .................................. 251/342; 251/354; 137/843; 604/48; 604/119; 604/902
[58] Field of Search ................ 251/342, 354; 137/843, 137/859, 877; 604/93, 118, 119, 902, 48

[56] References Cited

U.S. PATENT DOCUMENTS

| | | | |
|---|---|---|---|
| 2,674,262 | 4/1954 | Bradshaw | 137/859 X |
| 3,319,628 | 5/1967 | Halligan | 604/119 |
| 3,547,147 | 12/1970 | Shay | 251/354 X |
| 3,595,234 | 7/1971 | Jackson | 604/119 |
| 4,287,889 | 9/1981 | Stupar | 251/342 X |
| 4,356,823 | 11/1982 | Jackson | 604/119 |
| 4,420,101 | 12/1983 | O'Neill | 137/859 X |

*Primary Examiner*—A. Michael Chambers
*Assistant Examiner*—John C. Fox
*Attorney, Agent, or Firm*—Salter & Michaelson

[57] ABSTRACT

A suction control device for an aspirator system includes a generally T-shaped body having a main lumen and a passage which extends outwardly from the lumen to the exterior of the body through a vent or chimney portion of the body, and a resiliently deformable closure cap having one or more apertures therethrough which is received on the end of the chimney portion. The chimney portion is preferably formed with a flared terminal end, and the cap is resiliently depressible to a closed position wherein the apertured portion thereof is urged against the inner surface of the flared chimney portion end to obstruct the apertures in the cap and thereby close off the chimney portion. When the device is in the open position thereof, suction communication in the main lumen is interrupted by a venting effect through the chimney portion; and when the device is in its closed position, suction or negative pressure may be transmitted through the main lumen. By varying the degree of closure of the apertures, variable suction control may be achieved.

8 Claims, 5 Drawing Figures

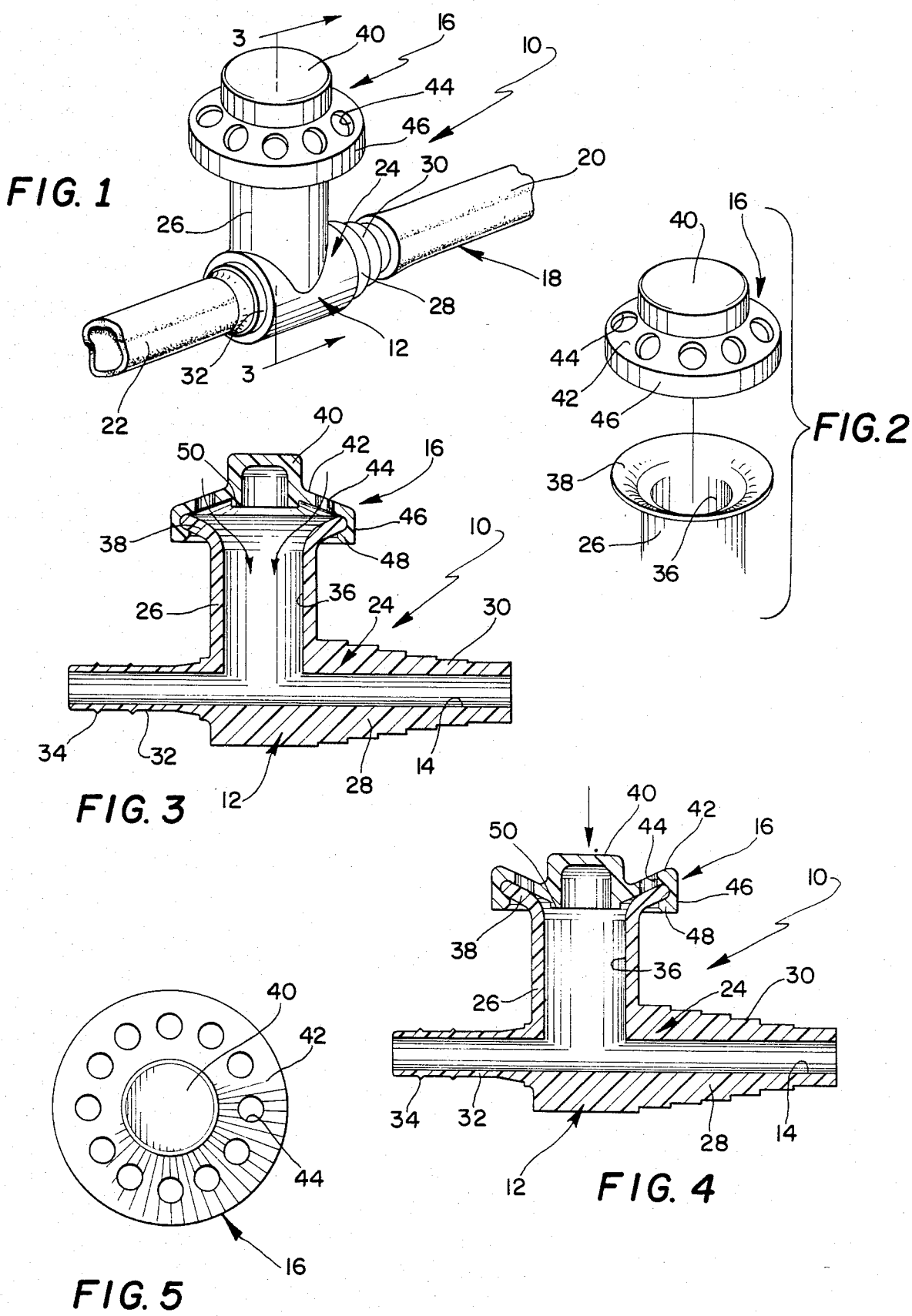

SUCTION CONTROL DEVICE FOR ASPIRATOR SYSTEM

BACKGROUND AND SUMMARY OF THE INVENTION

The instant invention relates to the medical field and more particularly to a suction control device for controlling the suction in an aspirator line of the type used for aspirating body fluids from a patient.

Aspirator lines are used for a wide variety of applications in medical practice, such as for suction catheters, surgical suction instruments, disposable bronchoscopes, surgical Yankauers, sigmoidoscopes, and suction Frazier instruments. Instruments of these types have required suction aspiration for the removal of sputum, mucus and/or other body fluids during various medical procedures. In each case, one end of an aspirator line is connected to a source of suction, and the other end of the line is introduced to a body cavity to effect the desired aspiration.

In order to effectively aspirate fluids from the human body, it is essential that some means be provided for adjusting and/or controlling the degree of suction which is applied through an aspirator line to an area of the human body. In many cases this is necessary in order to assure patient safety; and it is also frequently important for operator convenience. In particular, excessive suction can cause tissue damage to a patient in an aspirated area, and accordingly some type of suction control is important for patient safety. It is also substantially easier for a nurse, technician or physician to operate an aspirator if there is some simple means of controlling the suction level thereof. Heretofore, valves, such as stop cocks and the like, which are operative for on-off control, have been applied in medical aspirator applications; but they have not generally been effective for providing adjustable control for achieving varying degrees of suction. They have also not provided control means which is adapted for simple and convenient operation.

One of the more common simple devices heretofore available for controlling the suction in an aspirator line is a device commonly referred to as a T-piece. A conventional T-piece is of generally T-shaped configuration and comprises a main portion having a longitudinal main lumen therethrough, and a chimney portion which extends outwardly from the main portion and has a passage therethrough, the passage providing communication between the exterior of the device and the main lumen in the main portion. A conventional T-piece is receivable between two sections of an aspirator line so that the lumen in the main portion is in-line communication with the two line sections. Accordingly, the passage in the chimney portion provides an opening or a vent in the aspirator line so that vacuum communication through the T-piece is interrupted when the passage in the chimney portion is open to the atmosphere. On the other hand, by obstructing the flow of air through the passage in the chimney portion, this vent is closed so that vacuum communication can be transmitted through the main lumen in the T-piece. Therefore, a conventional T-piece is operable for on-off control of the vacuum in an aspirator line by manipulating a thumb or finger over the end of the passage in the chimney portion to alternately open or close the passage to thereby effect or interrupt vacuum communication through the lumen in the main portion of the device.

The most popular T-piece constructions theretofore available have been constructed so that the chimney portions thereof have outwardly flared terminal ends for receiving the thumbs or fingers of operators for alternately obstructing or opening the passages in the chimney portions thereof in the above manner.

While T-pieces of the above-described type have frequently been used for providing on-off control in aspirator lines used in medical applications, such devices have generally not been effective for achieving intermediate vacuum levels; and, in addition, such devices have often presented relatively unsanitary conditions for the operators thereof. Specifically, when a nurse, technician or physician operates a T-piece by placing a thumb over the end of the passage in the chimney portion thereof to effect vacuum in an aspirator line, mucus, sputum, or the like is conducted through the aspirator line and the longitudinal main lumen in the T-piece, and thereof quantities of such fluid may, at any given time, also be present in the T-piece passage and in contact with the operator's thumb or finger. When the operator's thumb is removed from the chimney portion of the T-piece, the spurting of sputum, mucus, or the like from the chimney portion may occur, causing further exposure of the operator. Potentially, diseases such as staph infections, strep throat, tuberculosis, or herpes can be transmitted in this manner; and hence it has generally been the practice for operators of T-tube type suction control devices to wear gloves in order to prevent direct exposure to disease carrying bodily fluids in this manner. Unfortunately, however, it has not been unusual for operators of T-tube type suction control devices to forget or neglect to wear gloves despite the potential hazards inherent in this practice.

The instant invention provides a novel control device for an aspirator line and the like which avoids the above-mentioned hazards and disadvantages of the heretofore-known devices. The device of the instant invention comprises a body which, in the preferred embodiment, comprises a conventional T-tube of the above-described type, and a cap portion which is received on the flared terminal end of the chimney portion of the body to provide a closure means which is depressible to a closed position wherein the end of the passage in the chimney portion is obstructed. In this regard, the cap portion preferably comprises an integrally molded member made of a rubberized material having a raised central button portion and an annular rim portion which extends outwardly from the button portion, the rim portion having a plurality of apertures therethrough and terminating in a peripheral flange which is secured to the outwardly flared terminal end of the chimney portion. The device is operative by depressing the button portion of the cap so that the inner surfaces of the rim portion are urged against the inner surfaces of the flared terminal end of the chimney portion, whereby the apertures in the rim portion are obstructed by the inner surfaces of the chimney portion, causing the passage in the chimney portion to be obstructed. Also in the preferred embodiment of the device, a splash-guard ring is provided on the inner side of the cap, the guard ring being disposed inwardly relative to the openings in the cap and being dimensioned and configured so that it extends into the chimney portion adjacent the wall thereof when the cap is in the closed position thereof, whereby the guard ring shields the openings in the cap from splashing from the chimney portion.

Accordingly, it is seen that the instant invention provides an effective device for controlling the degree of suction in an aspirator line without the aforementioned risks associated with the splashing or spurting of fluids from the heretofore-known T-tube type devices. While the device of the instant invention is not necessarily intended to eliminate the need for operators of aspirator devices to wear gloves, it substantially reduces the hazards associated with the failure to wear gloves. Further, the device of the instant invention provides an effective and convenient means for controlling the degree of suction in an aspirator line, and it also permits the operation of an aspirator line with various intermediate suction levels rather than merely fully-on or fully-off levels of suction.

It is therefore a primary object of the instant invention to provide an effective suction control device for an aspirator line.

Another object of the instant invention is to provide a closure cap which is operable in combination with a conventional T-tube for providing an effective and safe control for the operation of an aspirator line.

A still further object of the instant invention is to provide a simple suction control device which is operable for variable suction control at intermediate suction levels.

Other objects, features and advantages of the invention shall become apparent as the description thereof proceeds when considered in connection with the accommpanying illustrative drawings.

DESCRIPTION OF THE DRAWING

In the drawing which illustrates the best mode presently contemplated for carrying out the present invention:

FIG. 1 is a perspective view of the suction control device of the instant invention installed in an aspirator line;

FIG. 2 is an exploded perspective view of the flared terminal end of the chimney portion of the device and the closure cap;

FIG. 3 is a sectional view taken along line 3—3 in FIG. 1;

FIG. 4 is a similar view with the cap in the closed position thereof; and

FIG. 5 is a top plan view of the cap per se.

DESCRIPTION OF THE INVENTION

Referring now to the drawing, the suction control device of the instant invention is illustrated and generally indicated at 10 in FIGS. 1, 3 and 4. The control device 10 comprises a body generally indicated at 12 having a main lumen 14 therethrough, and a cap generally indicated at 16 which is received on the body 12. The device 10 is receivable in an aspirator line generally indicated at 18 having first and second portions 20 and 22, respectively, so that the lumen 14 extends therebetween. The device 10 is operable by manipulation of the cap 16 to effect or interrupt vacuum communication between the first and second portions 20 and 22, as well as to provide various intermediate degrees of vacuum communication therebetween.

The body 12 preferably comprises a conventional T-tube member of the type heretofore known and available for use in aspirator lines and comprises a main portion 24, through which the lumen 14 extends, and a chimney portion 26 which extends outwardly from the main portion 24. The main portion 24 preferably includes an outwardly extending first end 28 which is formed with a series of annular shoulders 30 of gradually reducing diameter, and an outwardly extending second end 32 having a plurality of annular ridges 34 thereon. The chimney portion 26 extends substantially perpendicularly outwardly from the main portion 24 and has an axial passage 36 therethrough which extends from the lumen 14 to the exterior of the body 12. The chimney portion 26 is preferably formed with an outwardly flared terminal end 38 as illustrated.

The cap 16 is preferably integrally molded of a suitable resiliently flexible or deformable rubberized material and preferably comprises a raised central button portion 40 of substantially circular configuration, a circular rim portion 42 which extends outwardly from the button portion 40, having a plurality of apertures 44 therethrough, and a circular flange portion 46 which extends downwardly from the rim portion 42, i.e., in a direction which is generally away from the button portion 40 and substantially parallel to the axis of the cap 16. The flange portion 46 is formed with an inner lip 48 adjacent the terminal end thereof, as illustrated in FIGS. 3 and 4, and a splash-guard ring 50 is integrally formed on the inner side of the cap 16, being inwardly disposed with respect to the apertures 44.

The cap 16 is received on the chimney portion 26 of the body 12 to provide a closure member for the passage 36. More specifically, the cap 16 is snap-received on the flared terminal end 38 so that the lip 48 engages the outer side of the flared end 38 to retain it within the flange 46 and thereby retain the cap 16 on the chimney portion 26. The cap 16 is preferably configured so that when it is received on the chimney portion 26 in this manner, the apertures 44 are disposed radially outwardly with respect to the main portion of the passage 36.

In operation of the device 10, the first and second end portions 30 and 32, respectively, are interconnected to the first and second aspirator line portions 20 and 22, respectively, so that the lumen 14 is in in-line communication therewith. In this regard, the first line portion 20 is connectable to a source of vacuum or suction, and the second line portion 22 is connectable to an aspirating instrument of the type which is directly operable for removing fluids from a patient. In the device 10, as herein embodied, the first end portion 30 is adapted for use with lines 20 of various sectional dimensions as a result of the shoulders 30; whereas the second end portion 32 is adapted to receive a line portion 22 of a predetermined dimension, the ridges 34 being provided to retain the line portion 22 on the end 32. It will be understood, however, that a variety of other constructions for the body 12 are contemplated. After the ends 30 and 32 have been connected to the line 18, the degree of suction transmitted through the device 10 from the first line portion 20 to the second line portion 22 is controllable by manipulating the device 10, in particular the cap 16 thereof. Specifically, when the cap 16 is in the normal, open position thereof illustrated in FIG. 3, suction transmitted to the device 10 through the first line portion 20 is interrupted by the inward flow of air through the apertures 44 into the passage 36; and therefore a venting action takes place which prevents the suction from the first line portion 20 from being transmitted through the main lumen 14 to the second line portion 22. However, the cap 16 may be moved to the closed position thereof illustrated in FIG. 4 by depressing the button portion 40 so that the apertures 44 are obstructed by the inner surface of the flared terminal end 38, whereby the cap 16 obstructs the outer end of the passage 36. Accordingly, the cap 16 provides a resiliently depressible closure member which obstructs or blocks the above-described venting action so that vacuum communication is transmitted from the first line portion 20 to the secoond line portion 22. Further, it will be seen that the device 10 is operable for achieving partial transmissions of vacuum from the first line portion 20 to the second line portion 22 by depressing the button portion 40 intermediate amounts so that the flow of air through the apertures 44 is merely restricted rather than completely shut off to provide partial venting effects. It will also be seen that the degree of vacuum transmitted between the line portions 20 and 22 can be easily changed by varying the degree to which the cap 40 is depressed.

The cap 16 effectively prevents the spurting or splashing of fluids aspirated through the line 22 from the chimney portion 26. In this regard, fluids passing outwardly through the chimney portion 26 normally engage the underside of the cap 16 so that they are prevented from reaching the apertures 44. This is because the apertures 44 are radially outwardly disposed with respect to the passage 36 so that fluids passing through the passage 36 impinge on the central portion of the cap 16 and do not reach the apertures 44. Further, in most instances, splashing within the chimney portion 26 occurs when the cap 16 is in an intermediate position after having been released from the closed position thereof illustrated in FIG. 4 so that a sudden change occurs in the vacuum level in the line portion 22. It will be seen that when the cap 16 is in the closed or depressed position thereof, the splash-guard ring 50 extends into the passage 36 slightly; and even when the cap is released to a partially closed position, the guard ring 50 extends at least somewhat into the flared terminal end 38; and therefore fluids splashing from the chimney portion 26 impinge on the ring 50 and are further prevented from reaching the apertures 44.

It is seen, therefore, that the instant invention provides an effective means for regulating the degree of suction in an aspirator line. The device 10 is operable in "on" or "off" positions, as well as in various positions to achieve various intermediate levels of suction as desired. Further, the device 10 effectively prevents splashing or spurting of aspirated fluids through the chimney portion 26; and therefore the device 10 has substantial advantages over the heretofore-known conventional open T-tube type devices. Accordingly, for these reasons, as well as the other reasons hereinabove set forth, it is seen that the device of the instant invention represents a significant improvement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A suction control device comprising a body having a main portion and an outwardly extending chimney portion, and a closure cap on said chimney portion, said main portion having a lumen therethrough, said chimney portion having a terminal end and having a passage therethrough which extends from said lumen to said terminal end, said terminal end having an annular closure surface thereon which extends outwardly from around the periphery of said passage, said closure cap being received on said terminal end and comprising an imperforate raised button portion and an annular rim portion which extends outwardly from said button portion, said rim portion having at least one aperture therethrough, said at least one aperture being disposed outwardly which respect to said passage, said cap being normally biased to an open position wherein said passage communicates with the exterior of said device through said at least one aperture, but being resiliently depressable to a closed position by manually depressing said button portion, said rim portion overlying said closure surface and said at least one aperture in said rim portion being obstructed by said closure surface to thereby obstruct said passage when said cap is in said closed position.

2. In the suction control device of claim 11, said closure means further characterized as being resiliently depressible to an intermediate position to partially obstruct said passage.

3. In the suction control device of claim 1, said closure means further characterized as being integrally molded from a resiliently deformable rubberized material.

4. In the suction control device of claim 1, said cap being snap-received on said terminal end.

5. In the suction control device of claim 1, said cap rim portion having a plurality of apertures therethrough which are disposed in spaced relation around said button portion, all of said apertures being disposed radially outwardly with respect to said passage and being obstructed by said closure surface when said cap is depressed to the closed position thereof to obstruct said passage.

6. In the suction control device of claim 1, said cap having a splash guard ring on the inner side thereof, said ring being disposed inwardly on said cap from said at least one aperture and extending into said chimney portion slightly when said closure cap is in the closed position thereof, said guard ring shielding said at least one aperture to prevent the splashing of fluids from said aspirator line through said passage.

7. A closure cap for an aspirator system of the type having an aspirator line and a chimney portion, which extends outwardly at an intermediate point in said aspirator line, said chimney portion having a passage therethrough which communicates with said line and terminating in a terminal end, said terminal end having an annular closure surface thereon which extends outwardly from around the periphery of said passage, said system being operative to communicate suction in said line past said chimney portion by obstructing the passage in said chimney portion, said cap comprising an imperforate raised button portion and an annular rim portion which extends outwardly from said button portion and has at least one aperture therethrough, said cap being securable on said terminal end so that said at least one aperture is disposed outwardly with respect to said passage and being resiliently deformable to a closed position by manually depressing said button portion, said rim portion overlying said closure surface and said at least one aperture in said rim portion being obstructed by said closure surface to thereby obstruct said passage when said cap is in said closed position.

8. The cap of claim 7 further characterized as being snap-receivable on said chimney terminal end.

* * * * *